(12) United States Patent
De Vries

(10) Patent No.: US 7,478,445 B2
(45) Date of Patent: Jan. 20, 2009

(54) RECLINING TABLE WITH AN ADJUSTABLE BACK REST

(75) Inventor: Bram De Vries, Goudriaan (NL)

(73) Assignee: Sinmed Holding International B.V. (NL)

( * ) Notice: Subject to any disclaimer, the term of this patent is extended or adjusted under 35 U.S.C. 154(b) by 0 days.

(21) Appl. No.: 11/850,124

(22) Filed: Sep. 5, 2007

(65) Prior Publication Data

US 2008/0052829 A1 Mar. 6, 2008

(30) Foreign Application Priority Data

Sep. 6, 2006 (NL) .................................... 1032453

(51) Int. Cl.
*A61G 13/12* (2006.01)
*A47C 20/00* (2006.01)

(52) U.S. Cl. .................................... 5/601; 5/622; 5/634

(58) Field of Classification Search ............... 5/601, 5/600, 612, 613, 617, 621, 622, 630, 632–634, 5/640, 657, 659, 660; 378/208, 209; 297/377
See application file for complete search history.

(56) References Cited

U.S. PATENT DOCUMENTS

| | | | | |
|---|---|---|---|---|
| 5,100 A | * | 5/1847 | Latourandais .................. | 5/618 |
| 6,594 A | * | 7/1849 | Linikin ........................ | 297/108 |
| 39,462 A | * | 8/1863 | Brown .......................... | 5/634 |
| 56,211 A | * | 7/1866 | Guyer .......................... | 5/618 |
| 163,684 A | * | 5/1875 | Ogborn et al. ................. | 5/617 |
| 224,272 A | * | 2/1880 | Buell .......................... | 297/118 |
| 238,780 A | * | 3/1881 | Hopkins et al. ................ | 5/634 |
| 254,149 A | * | 2/1882 | Mott, Jr. ..................... | 5/618 |
| 306,590 A | * | 10/1884 | Davis .......................... | 5/622 |
| 309,678 A | * | 12/1884 | Aubin ......................... | 606/241 |
| 313,743 A | * | 3/1885 | Lariew ........................ | 5/617 |
| 318,368 A | * | 5/1885 | Gitt ........................... | 297/408 |
| 319,537 A | * | 6/1885 | Winter ......................... | 5/634 |
| 374,804 A | * | 12/1887 | Nicholas ....................... | 5/634 |
| 579,660 A | * | 3/1897 | Williamson et al. ............. | 5/634 |
| 603,756 A | * | 5/1898 | Drawe ......................... | 5/634 |

(Continued)

FOREIGN PATENT DOCUMENTS

DE        3809380        9/1989

OTHER PUBLICATIONS

European Search Report, for corresponding Application No. EP07075758, dated Jan. 4, 2008.

*Primary Examiner*—Robert G Santos
(74) *Attorney, Agent, or Firm*—Caesar, Rivise, Bernstein, Cohen & Pokotilow, Ltd.

(57) ABSTRACT

A reclining table comprising a stationary reclining plate and a back rest pivotally connected to it. A supporting member pivotally connected to said reclining plate near its free end serves for supporting said back rest in various angular positions. Said supporting member has a number of lateral slots for receiving lips of a supporting plate being pivotally connected to said back rest and in that case engaging said back rest. The supporting member is able to support the back rest at an angle of 15° at the most, for example. Beyond that, said supporting plate can be used, which will then cooperate with grooves provided on the reclining plate for supporting the back rest at angles larger than the maximum angle first mentioned. Supporting member and supporting plate are collapsed onto the reclining plate when said back rest is to be brought to the horizontal position.

7 Claims, 2 Drawing Sheets

U.S. PATENT DOCUMENTS

| | | | | |
|---|---|---|---|---|
| 676,765 | A | * | 6/1901 | Nincehelser .................... 5/634 |
| 691,224 | A | * | 1/1902 | Wilkins ......................... 5/634 |
| 696,425 | A | * | 4/1902 | Farr ............................ 297/372 |
| 858,908 | A | * | 7/1907 | Rauch ........................... 5/634 |
| 966,637 | A | * | 8/1910 | Akin ............................ 5/634 |
| 969,099 | A | * | 8/1910 | Fuchs ........................... 5/634 |
| 989,888 | A | * | 4/1911 | Adler ............................ 5/634 |
| 1,003,982 | A | * | 9/1911 | Butler ........................... 5/634 |
| 1,103,730 | A | * | 7/1914 | Anderson ....................... 5/634 |
| 1,151,894 | A | * | 8/1915 | Meinecke ....................... 5/634 |
| 1,218,519 | A | * | 3/1917 | Bradley ......................... 5/618 |
| 1,281,074 | A | * | 10/1918 | Russell ......................... 5/634 |
| 1,297,088 | A | * | 3/1919 | Butler ........................... 5/634 |
| 1,447,486 | A | * | 3/1923 | Schafer et al. ............... 297/351 |
| 1,514,202 | A | * | 11/1924 | Davenport ..................... 5/634 |
| 1,515,886 | A | * | 11/1924 | Rumsey ......................... 27/13 |
| 1,632,160 | A | * | 6/1927 | Barnes .......................... 27/13 |
| 1,706,579 | A | * | 3/1929 | Martin .......................... 5/617 |
| 1,902,249 | A | * | 3/1933 | Lanzy ........................... 5/617 |
| 2,074,653 | A | * | 3/1937 | Larsen .......................... 297/372 |
| 2,133,223 | A | * | 10/1938 | Brightman et al. ............. 5/634 |
| 2,208,945 | A | * | 7/1940 | Miller .......................... 297/170 |
| 2,250,026 | A | * | 7/1941 | Laukhuff ....................... 5/634 |
| 2,368,436 | A | * | 1/1945 | Williams ....................... 5/634 |
| 2,387,357 | A | * | 10/1945 | Rogerson ....................... 5/660 |
| 2,429,795 | A | * | 10/1947 | Blanchard et al. ........... 297/118 |
| 2,563,671 | A | * | 8/1951 | Basinger ....................... 248/456 |
| 2,614,271 | A | * | 10/1952 | Neil ............................. 5/640 |
| 2,663,029 | A | * | 12/1953 | Whitley et al. ................. 5/634 |
| 2,666,216 | A | * | 1/1954 | Schnaitter ...................... 5/660 |
| 2,697,480 | A | * | 12/1954 | Du Bois et al. ............. 297/325 |
| 2,738,249 | A | * | 3/1956 | Tenenblatt ................... 312/237 |
| 2,777,138 | A | * | 1/1957 | Gallagher ...................... 5/655 |
| 2,788,529 | A | * | 4/1957 | Moritzacky et al. ........... 5/634 |
| 2,817,857 | A | * | 12/1957 | Hockensmith ................. 5/640 |
| 2,884,991 | A | * | 5/1959 | Bloomquist .................. 297/377 |
| 2,918,682 | A | * | 12/1959 | Thoresen et al. ............... 5/660 |
| 3,101,972 | A | * | 8/1963 | Laughlin ..................... 297/377 |
| 3,171,687 | A | * | 3/1965 | Jensen ........................ 297/377 |
| 3,211,495 | A | * | 10/1965 | Nielsen ........................ 297/68 |
| 3,276,817 | A | * | 10/1966 | Marple ........................ 297/377 |
| 3,289,222 | A | * | 12/1966 | Nielsen ........................ 5/617 |
| 3,329,979 | A | * | 7/1967 | Drapin ........................ 5/634 |
| 3,334,944 | A | * | 8/1967 | Gould et al. ................. 297/377 |
| 3,423,773 | A | * | 1/1969 | Yamate ........................ 5/610 |
| 3,452,372 | A | * | 7/1969 | Emery ........................ 5/634 |
| 3,484,878 | A | * | 12/1969 | Nielsen ........................ 5/617 |
| 3,556,587 | A | * | 1/1971 | Rymes ........................ 297/133 |
| 3,774,247 | A | * | 11/1973 | Bradley ........................ 5/53.2 |
| 3,790,973 | A | * | 2/1974 | Bradley ........................ 5/53.2 |
| 3,800,338 | A | * | 4/1974 | Smith ........................ 5/617 |
| 4,074,374 | A | * | 2/1978 | Ayesh ........................ 5/400 |
| 4,218,788 | A | * | 8/1980 | Steckmesser ................. 5/617 |
| 4,266,759 | A | * | 5/1981 | Liebman ........................ 5/632 |
| 4,346,487 | A | * | 8/1982 | Holdt et al. .................... 5/617 |
| 4,660,237 | A | * | 4/1987 | Brodnax ....................... 5/636 |
| 4,754,507 | A | * | 7/1988 | Edge ............................ 5/633 |
| 5,029,349 | A | * | 7/1991 | Hamilton ....................... 5/111 |
| 5,127,422 | A | * | 7/1992 | Colon .......................... 5/655 |
| 5,160,185 | A | * | 11/1992 | Stang ........................ 297/377 |
| 5,553,921 | A | * | 9/1996 | Schenk ........................ 297/352 |
| 5,926,876 | A | | 7/1999 | Haigh et al. |
| 6,003,174 | A | | 12/1999 | Kantrowitz et al. |
| 6,029,669 | A | * | 2/2000 | Hammock ................. 128/845 |
| 6,139,567 | A | * | 10/2000 | McCarty et al. ............. 606/237 |
| 6,561,582 | B1 | * | 5/2003 | Steadman ................ 297/250.1 |
| 6,684,431 | B2 | * | 2/2004 | Splane, Jr. .................... 5/657 |
| 7,201,170 | B2 | * | 4/2007 | Espinosa .................. 128/845 |
| 7,275,273 | B2 | * | 10/2007 | Lary et al. .................... 5/634 |
| 2003/0084513 | A1 | * | 5/2003 | Splane ......................... 5/657 |
| 2005/0085722 | A1 | | 4/2005 | Waterman |
| 2005/0251918 | A1 | * | 11/2005 | Lary et al. .................... 5/634 |
| 2008/0052829 | A1 | * | 3/2008 | De Vries ........................ 5/601 |

* cited by examiner

RECLINING TABLE WITH AN ADJUSTABLE BACK REST

CROSS-REFERENCE TO RELATED APPLICATIONS

This application claims priority under 35 U.S.C. §119(a) of Dutch Application No. 1032453, filed Sep. 6, 2006.

SPECIFICATION

BACKGROUND OF THE INVENTION

1. Field of the Invention

The invention relates to a reclining table comprising a stationary reclining plate and a back rest pivotally connected to it, with means being provided for supporting the back rest in a number of angular positions in relation to the reclining plate.

2. Description of Related Art

Such a reclining table is known from U.S. Pat. No. 6,003, 174. This concerns a reclining table for a patient whose head is to be examined in a scanning device. There, the back rest is connected to a pivot shaft, which is rotatably supported by the reclining plate. With this reclining plate gear wheels are connected having their axes coinciding with the axis of the pivot shaft. The back rest is provided with spring-biased pins, each being pushed into one of the teeth of the accompanying gear wheel in order to support the pivot shaft and with it, the back rest, in a certain position.

For adjusting the back rest, the pins must be pulled out of the teeth of the gear wheels, which is effected by a rod extending parallel to the pivot shaft being connected to the back rest.

It is obvious, that considerable forces are exerted on the pivot shaft, and thus on the pins as well. The structure must be designed for this and is therefore relatively heavy and complicated. Nevertheless it is suited for the intended purpose, since the patient's head must be brought into a relatively small opening of the device concerned.

BRIEF SUMMARY OF THE INVENTION

The object of the invention is to provide a reclining table of the above-mentioned type which is simple in construction and easy to operate.

According to the invention, to that end, the reclining plate of the reclining table is provided with a supporting member which is pivotally connected to the reclining plate near the location where the free end of the back rest will be positioned near the free end of the reclining plate when the back rest is in the almost horizontal position, said supporting member being provided with means for supporting the back rest in a number of angular positions up to a maximum angular position, and in which said supporting member can be folded down onto the reclining plate when not in use, and further a supporting plate is provided, which is pivotally connected to the back rest in a position spaced from its free end and which can cooperate with said means provided on the reclining plate for supporting the back rest in a number of angles, said angles being greater than the first-mentioned, maximum angle, and in which said supporting plate can be pivoted against the back rest.

In this way, it is achieved, that both of the supporting member and the supporting plate can be pivoted against the reclining plate and the back rest, respectively, in such a way that the back rest can take up the almost horizontal position, if desired.

With the structure according to the invention, it is also achieved, that the supporting member can be of a relatively limited length. Namely, the supporting member only has to support the back rest across a relatively small angle. Should the back rest have to be adjusted across a greater angle, then the supporting member will be folded down and its function will be taken over by the supporting plate.

This can be particularly important when the reclining table with the back rest is used in examining a patient by means of X-rays or other similar rays. There, it is desirable, that the radiation is hindered as less as possible by parts of the structure on which the patient lies.

The relatively limited length of the supporting member will generally allow it to be outside the area of the radiation in the collapsed state, too.

According to the invention, it can be particularly provided for, that the means cooperating with the supporting member, during its use, will extend beyond the free end edge of the back rest.

When the back rest is adjusted to relatively small angles by means of the supporting member, the supporting member will project beyond the back rest. In order to limit the distance across which the supporting member projects beyond the back rest, said supporting member, after achieving the maximum angle, will be pivoted onto the reclining plate. For adjusting the back rest to a greater angle, one will then switch over to use of the supporting plate.

In particular, the supporting plate can be provided with the means that can cooperate with the supporting member, said means extending outside the back rest when the supporting plate has been pivoted against the back rest, in such a way that the free end edge of the supporting plate is near the free end edge of the back rest.

The means allowing for the cooperation between the supporting member and the supporting plate can be formed by lateral slots provided in the supporting member and lips connected to the free end of the supporting plate which can be received in the lateral slots.

The means mounted on the reclining plate for supporting the back rest across a number of angles can be formed by a number of slots provided behind one another across the length of the reclining plate, in which the free end edge of the supporting plate can be received.

In particular, the slots will be provided in pairs and spaced-apart, in such a way that the lips connected to the supporting plate will be able to cooperate with the slots when using the supporting plate.

In order to avoid weakening of the reclining plate, the slots will be provided in blocks, that are fastened onto the reclining plate, said blocks being at such a distance from one another, that the supporting member can lie between them, the width of the lips connected to the supporting plate being such, that they can cooperate with both the supporting member and said slots.

BRIEF DESCRIPTION OF SEVERAL VIEWS OF THE DRAWING

The invention will now be explained further by way of an embodiment, illustrated in the drawings, in which.

DETAILED DESCRIPTION OF THE PREFERRED EMBODIMENT

Figure 1:
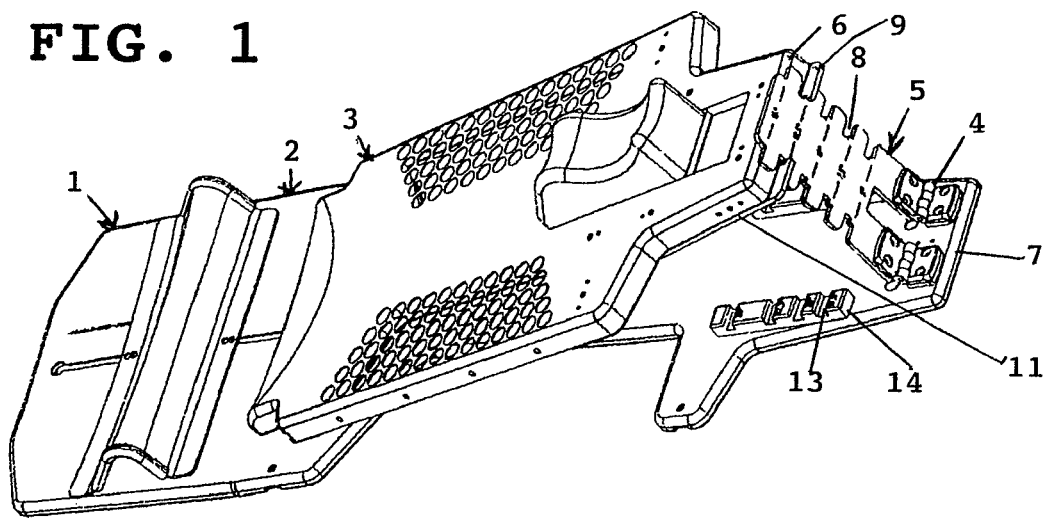
FIG. 1 shows a perspective view of a part of a reclining table according to the invention, which particularly shows the part having the adjustable back rest, the back rest taking up a certain angle with the help of the supporting member.

The reclining table 1, shown only partly in the drawings, comprises a stationary reclining plate 2 and a back rest 3 pivotally connected to it. The reclining plate 2 can be part of the reclining table 1 or can be connected to it.

By means of pivots 4, a supporting member 5 is connected to the reclining plate 2 near the location where the free end 6 of the back rest 3 will be situated near the free end 7 of the reclining plate 2 when the back rest 3 is in its almost horizontal position.

Figure 2:
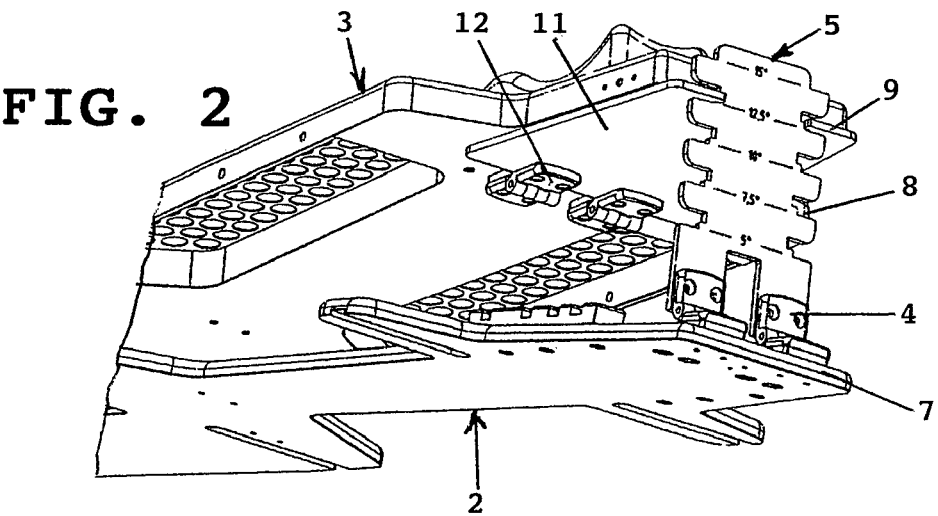
FIG. 2 shows a perspective view according to FIG. 1, yet seen from a lower position.

As appears in particular from FIGS. 1 and 2, said supporting member 5 is provided with lateral slots 8 into which lips 9 provided at the free end edge 10 of a supporting plate 11, can be received. Supporting plate 11 is connected to the back rest 3 by means of pivots 12.

FIG. 2 shows that said supporting member 5 can cooperate with supporting plate 11 in such a way, that the back rest 3 can be adjusted to a first angle of 5° and in subsequent steps of 2,5°. The maximum angle will be 15°.

Figure 3:
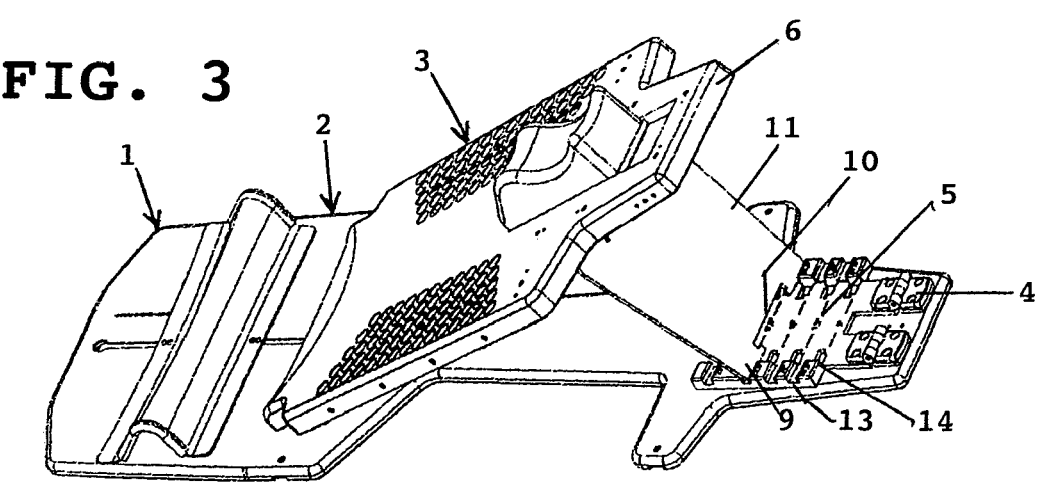
FIG. 3 shows a perspective view with the back rest in a certain angle with the help of the supporting plate.

When one wishes to adjust the back rest 3 at an angle greater than 15°, use is made of the supporting plate 11 and the supporting member 5 is folded down onto the reclining plate 2 as illustrated in FIG. 3.

As likewise shown in FIG. 3, lips 9 connected to the supporting plate 11 are now received in slots 13, which are provided in blocks 14 connected to the reclining plate 2. The mutual distance between the blocks 13 is such, that the back rest 3 is adjustable across subsequent almost equal angles.

Figure 4:
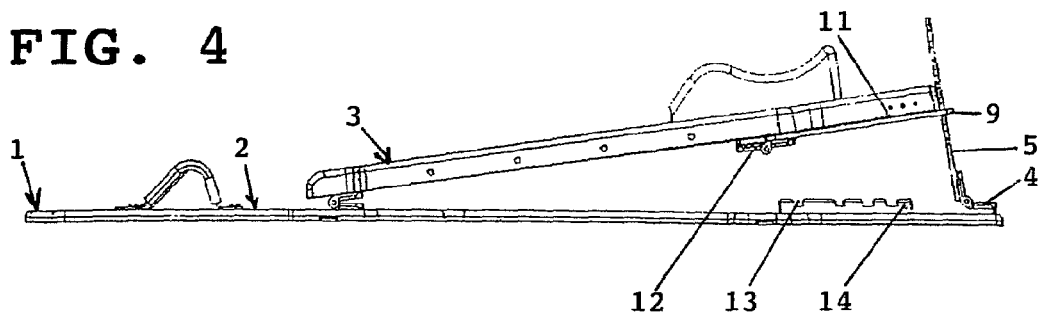
FIGS. 4 and 5 show side views of the reclining table in which the back rest is held in two different angles using the supporting member.
Figure 5:
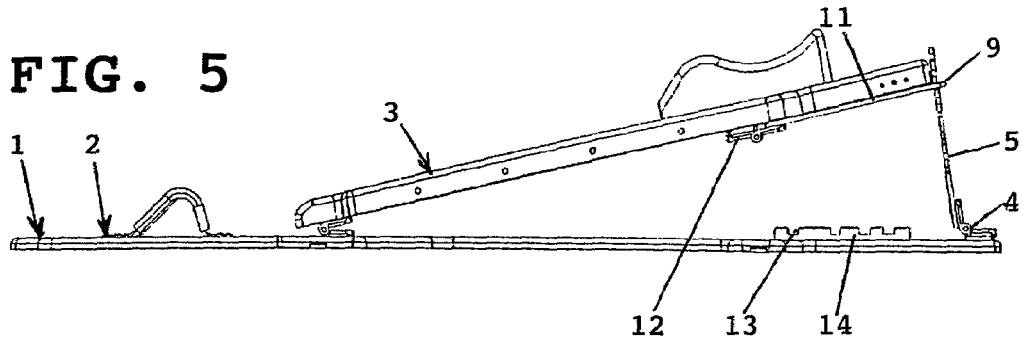

FIGS. 4 and 5 illustrate two different angular positions of the back rest 3 using the supporting member 5. Now said lateral slots 8 of supporting member 5 cooperate with the lips 9 of the supporting plate 11.

Figure 6:
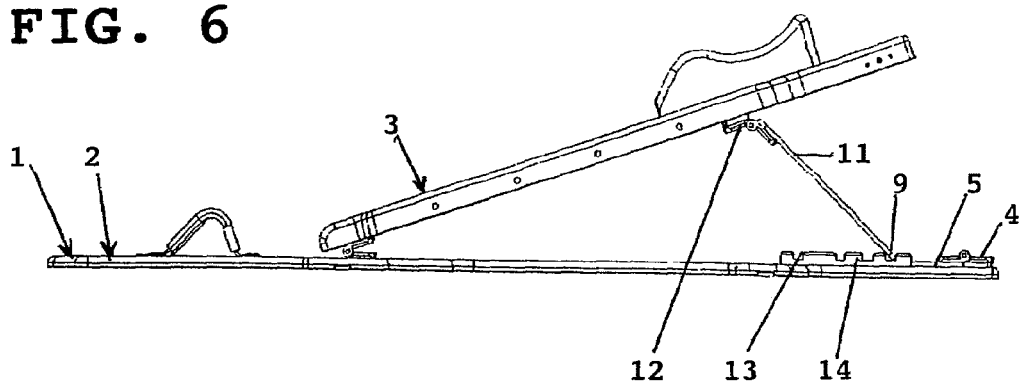
FIGS. 6 and 7 show side views of the reclining table in which the back rest is held in two different angles using the supporting plate.
Figure 7:
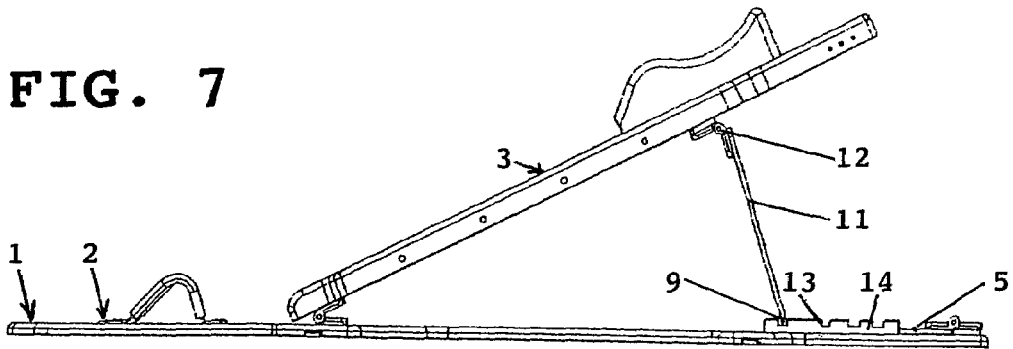

FIGS. 6 and 7 show two different angular positions of the back rest 3 using the supporting plate 11, its lips 9 cooperating with the slots 13 in the blocks 14.

When the back rest 3 must be brought into the most horizontal position, the supporting plate 11 will be pivoted from the position shown in FIGS. 1 and 2, in such a way, that it will engage the other part of the back rest.

Although above, a "reclining table" is discussed, it might also be of a limited length. Thus, then one could think of a reclining chair.

It will be obvious, that only one exemplary embodiment of a reclining table with back rest according to the invention is shown in the drawing and described above and that many modifications can be made without leaving the scope of the invention, as this is indicated in the claims.

What is claimed is:

1. A reclining table comprising a stationary reclining plate, a back rest, a supporting plate and supporting means, said stationary reclining plate having a free end, said back rest being pivotally connected to said reclining plate and having a free end, said supporting means being provided on said reclining plate for supporting said back rest in a number of angular positions up to a first maximum angular position in relation to said reclining plate, said supporting means comprising a first supporting member and a second supporting member, said first supporting member being pivotally connected to said reclining plate near the location where said free end of said back rest will be positioned near said free end of said reclining plate when said back rest is in an almost horizontal position, said second supporting member comprising plural slots fixedly connected to and located on said reclining plate, said first supporting member being arranged to be folded down onto said reclining plate when not in use, said supporting plate being pivotally connected to said back rest in a position spaced-apart from said free end of said back rest and being arranged to cooperate with respective ones of said plural slots of said second supporting member for supporting said back rest in a number of angular positions up to a second maximum angular position, said second maximum angular position being greater than said first maximum angular position.

2. The reclining table according to claim 1, wherein said supporting plate in use projects beyond said free end edge of said back rest.

3. The reclining table according to claim 1, wherein said first supporting member comprises plural slots and wherein said supporting plate comprises at least one lip which is arranged to be located within any one of said plural slots in said first supporting member.

4. The reclining table according to claim 1, wherein said supporting plate comprises at least one lip which is arranged to be located within any one of said plural slots of said second supporting member.

5. The reclining table according to claim 3, wherein said at least one lip comprises a free edge, said free edge being arranged to be received within any of said plural slots of said second supporting member, said plural slots of said second supporting member being provided behind one another in the length of said reclining plate.

6. The reclining table according to claim 5, wherein said supporting plate comprises two lips, each having a free edge, and wherein said plural slots of said second supporting member are provided in pairs and spaced-apart laterally, in such a way that said lips of said supporting plate are receivable in any of said pairs of spaced-apart slots of said second supporting member when using said supporting plate.

7. The reclining table according to claim 6, wherein said pairs of spaced-apart slots are provided in blocks fastened on said reclining plate, said blocks being at such distance from one another, that said first supporting member can lie between them, while the width of said lips is such that said lips can cooperate with said slots of said first supporting member and with said slots of said second supporting member.

* * * * *